United States Patent
Chen et al.

(10) Patent No.: US 12,292,563 B2
(45) Date of Patent: May 6, 2025

(54) ENDOSCOPE SYSTEM HAVING A DISPLAY CONTROL APPARATUS, A DETECTION APPARATUS, AND A PROBE

(71) Applicant: AUTEL INTELLIGENT TECHNOLOGY CORP., LTD., Guangdong (CN)

(72) Inventors: Huaming Chen, Guangdong (CN); Yuanping Luo, Guangdong (CN); Runbin Wang, Guangdong (CN)

(73) Assignee: AUTEL INTELLIGENT TECHNOLOGY CORP., LTD., Shenzhen (CN)

( * ) Notice: Subject to any disclaimer, the term of this patent is extended or adjusted under 35 U.S.C. 154(b) by 499 days.

(21) Appl. No.: 17/658,866

(22) Filed: Apr. 12, 2022

(65) Prior Publication Data

US 2022/0236554 A1   Jul. 28, 2022

Related U.S. Application Data

(63) Continuation of application No. PCT/CN2020/120443, filed on Oct. 12, 2020.

(30) Foreign Application Priority Data

Oct. 18, 2019 (CN) .......................... 201910995157.5

(51) Int. Cl.
*G02B 23/24* (2006.01)
*A61B 1/00* (2006.01)
(Continued)

(52) U.S. Cl.
CPC ...... *G02B 23/2446* (2013.01); *A61B 1/00016* (2013.01); *A61B 1/00032* (2013.01);
(Continued)

(58) Field of Classification Search
None
See application file for complete search history.

(56) References Cited

U.S. PATENT DOCUMENTS

| | | | |
|---|---|---|---|
| 5,282,030 A * | 1/1994 | Nishimura | H04N 25/135 |
| | | | 375/240.18 |
| 2002/0067408 A1 * | 6/2002 | Adair | H04N 23/66 |
| | | | 348/66 |

(Continued)

FOREIGN PATENT DOCUMENTS

| | | |
|---|---|---|
| CN | 101860726 A | 10/2010 |
| CN | 101990088 A | 3/2011 |

(Continued)

OTHER PUBLICATIONS

First office action of CN patent application No. 201910995157.5 issued on Apr. 2, 2024.

(Continued)

*Primary Examiner* — John P Leubecker
(74) *Attorney, Agent, or Firm* — Andrew C. Cheng

(57) ABSTRACT

An endoscope system applied to vehicle diagnosis equipments is provided. The endoscope system includes a display control apparatus, a detection apparatus and a probe. The detection apparatus is respectively in communication connection with the display control apparatus and the probe. The probe is configured to collect image information of an internal device of a vehicle and send the image information to the detection apparatus. The detection apparatus is configured to send the image information to the display control apparatus. The display control apparatus is configured to display the image information. The endoscope system can realize wireless remote transmission of image information, can realize the separate operation of image display and image detection, and can realize a convenient, accurate and (Continued)

highly efficient vehicle fault diagnosis operation while facilitating mobile operation thereof.

12 Claims, 5 Drawing Sheets

(51) Int. Cl.
*A61B 1/06* (2006.01)
*A61B 1/12* (2006.01)
*H04N 23/60* (2023.01)

(52) U.S. Cl.
CPC ...... *A61B 1/00181* (2013.01); *G02B 23/2461* (2013.01); *G02B 23/2484* (2013.01); *H04N 23/60* (2023.01); *A61B 1/0684* (2013.01); *A61B 1/128* (2013.01)

(56) References Cited

U.S. PATENT DOCUMENTS

| | | | | |
|---|---|---|---|---|
| 2002/0184122 A1* | 12/2002 | Yamaguchi | ............ | G07F 17/04 705/30 |
| 2003/0004397 A1* | 1/2003 | Kameya | ............ | A61B 1/05 600/101 |
| 2003/0228553 A1* | 12/2003 | Mandelkern | ......... | A61B 1/0676 433/29 |
| 2005/0091431 A1* | 4/2005 | Olodort | ............ | H04M 1/0245 710/72 |
| 2008/0195128 A1* | 8/2008 | Orbay | ............ | A61B 1/00048 600/183 |
| 2011/0190595 A1* | 8/2011 | Bennett | ............ | A61B 1/05 600/300 |
| 2011/0193949 A1* | 8/2011 | Nambakam | ............ | A61B 17/00 348/E7.085 |
| 2012/0035418 A1* | 2/2012 | Talbert | ............ | A61B 1/00016 600/109 |
| 2013/0096382 A1* | 4/2013 | Alexander | ......... | A61B 1/00142 600/110 |
| 2014/0146142 A1* | 5/2014 | Duret | ............ | A61C 19/04 348/46 |
| 2019/0356829 A1* | 11/2019 | Sidar | ............ | A61B 1/0638 |
| 2022/0395160 A1* | 12/2022 | Salman | ............ | A61B 1/0669 |

FOREIGN PATENT DOCUMENTS

| | | |
|---|---|---|
| CN | 202948200 U | 5/2013 |
| CN | 203606564 U | 5/2014 |
| CN | 104173018 A | 12/2014 |
| CN | 205322284 U | 6/2016 |
| CN | 107065169 A | 8/2017 |
| CN | 108693191 A | 10/2018 |
| CN | 208079245 U | 11/2018 |
| CN | 208798094 U | 4/2019 |
| CN | 110687672 A | 1/2020 |
| CN | 210982906 U | 7/2020 |
| WO | 2014063042 A1 | 4/2014 |

OTHER PUBLICATIONS

Search report of CN patent application of No. 201910995157.5 issued on Apr. 2, 2024.
International search report of PCT/CN2020/120443 mailed Jan. 14, 2021.

* cited by examiner

ENDOSCOPE SYSTEM HAVING A DISPLAY CONTROL APPARATUS, A DETECTION APPARATUS, AND A PROBE

CROSS REFERENCE TO RELATED APPLICATIONS

The present application is continuation application of International Application No. PCT/CN2020/120443, filed on Oct. 12, 2020, which claims priority to the Chinese patent application No. 201910995157.5 filed on Oct. 18, 2019, which are incorporated herein by reference in its entirety.

BACKGROUND

Technical Field

The present application relates to the technical field of endoscopes, and more particularly to an endoscope system.

Related Art

An endoscope is a kind of equipment used to observe an area that can not be directly observed by human eyes. For example, it is commonly used in the maintenance and repair of vehicles in the industrial field. In order to detect the complex mechanism environment inside vehicles, observe the high-temperature parts of vehicles and the parts which can not be directly seen by human eyes, and realize the non-destructive detection without disassembling or damaging parts, modules, etc., it is necessary to use an industrial endoscope as a detection tool to monitor, photograph, video, etc. so as to find the cracks, wear, blockage and suspicious components through image analysis, which provides an important reference for the diagnosis of vehicle fault.

At present, the commonly used endoscope is mainly composed of the endoscope body, liquid crystal display, camera cabin, probe, probe head, and like components. These mechanical structures are integrated, with features of compact structure, small volume, being easy to carry, etc. When using an endoscope to detect a vehicle fault, an endoscope is generally used to acquire image data of a complex mechanism environment inside the vehicle and then upload the same to other terminal equipment (such as a computer) so that a technician can perform fault diagnosis on the vehicle according to the image data.

However, the related art has at least the following problems. There is a problem of poor convenience and low efficiency in vehicle fault diagnosis according to the existing endoscope system.

SUMMARY

The technical problem to be solved by the present application is to provide an endoscope system to achieve the convenience, accuracy, and high efficiency of vehicle fault diagnosis.

To solve the above technical problem, embodiments of the present application provide the following technical solutions. An endoscope system applied to vehicle diagnosis equipments is provided, the endoscope system comprising a display control apparatus, a detection apparatus, and a probe, wherein the detection apparatus is communicatively connected with the display control apparatus and the probe respectively.

The probe is configured to collect image information of an internal device of a vehicle and sending the image information to the detection apparatus. The detection apparatus is configured to send the image information to the display control apparatus. The display control apparatus is configured to display the image information.

The display control apparatus comprises a first wireless communication module, and the detection apparatus comprises a second wireless communication module and a first probe joint. The display control apparatus is communicatively connected to the second wireless communication module of the detection apparatus via the first wireless communication module, and the detection apparatus is communicatively connected to the probe via the first probe joint.

The first wireless communication module and the second wireless communication module are WIFI modules and the first probe joint is a USB interface.

The display control apparatus comprises a housing, a control module is provided in the housing, a display module is provided on the housing, and the control module is electrically connected to the display module.

The control module is configured to control the display module to display the image information.

The control module comprises a controller, a memory, and a power supply system. The memory is communicatively connected to the controller via a bus, the power supply system is electrically connected to the controller.

The controller is configured to control the display module to display the image information sent by the detection apparatus.

The display control apparatus further comprises an input module, a battery module, a fixing module, a camera, a storage module, a USB interface, a multimedia interface, a light sensing module, an indicator lamp, an interaction module, and a direction sensor.

The battery module, the storage module, the light sensing module, and the direction sensor are arranged in the housing and are respectively electrically connected to the control module. The fixing module is arranged on an outer surface of the housing. The input module, the camera, the USB interface, the multimedia interface, the indicator lamp, and the interaction module are arranged on the housing and are electrically connected to the control module respectively.

The input module is configured to receive an input operation of a user. The battery module is configured to supply power to the display control apparatus. The fixing module is configured to fix the display control apparatus. The camera is configured to collect information of an environment where the display control apparatus is currently located. The storage module is configured to store the image information. The USB interface is configured to transmit the image information to third-party equipment. The multimedia interface is configured to connect third-party display equipment. The light sensing module is configured to detect brightness of ambient light, the indicator lamp is configured to reminding the user of state-of-charge of the battery module. The interaction module is configured to realize interaction between the display control apparatus and the user, and the direction sensor is configured to detect a display state of the display module.

The detection apparatus further comprises a control module. The control module is connected to the first probe joint and configured to acquire the image information via the first probe joint.

The control module comprises a controller, a memory, and a power supply system. The memory is communicatively connected to the controller via a bus, and the power supply system is electrically connected to the controller.

The detection apparatus further comprises a battery module, an air cooling system, an LED light, and a key. The battery module, the air cooling system, the LED light, and the key are respectively electrically connected to the control module.

The battery module is configured to supply power to the detection apparatus. The air cooling system is configured to provide a cooling service for the detection apparatus. The LED light is configured to provide ambient lighting, and the key is configured to receiving an operation of a user to realize interactive functions of photographing, video recording, and storing.

The probe is provided with a first camera and a second camera. The first camera is correspondingly provided with an LED fill lamp, and the second camera is correspondingly provided with another LED fill lamp. The probe further comprises a controller and a second probe joint, the controller is respectively electrically connected to the first camera, the second camera, two LED fill lamps, and the second probe joint.

The controller is configured to control the first camera and the second camera to collect the image information, adjust the brightness of the two LED fill lamps according to the environment, and transmit the image information to the detection apparatus via the second probe joint.

The embodiments of the present application provide an endoscope system, which is different from a traditional industrial endoscope in that the display control apparatus, the detection apparatus, and the probe are divided into three parts, wherein the display control apparatus is in wireless communication connection with the detection apparatus, and the detection apparatus is in communication connection with the probe. The endoscope system can realize wireless remote transmission of image information, can realize the separate operation of image display and image detection, and can realize a convenient, accurate, and highly efficient vehicle fault diagnosis operation while facilitating mobile operation thereof.

BRIEF DESCRIPTION OF THE DRAWINGS

One or more embodiments are exemplified by the accompanying drawings corresponding thereto. These exemplified descriptions do not constitute a limitation on the embodiments. Elements in the drawings having the same reference number designations are illustrated as similar elements, and unless otherwise particularly stated, the drawings do not constitute a proportional limitation.

DETAILED DESCRIPTION

To facilitate the understanding of the present application, a more detailed description will be rendered below by reference to the accompanying drawings and specific embodiments. It needs to be noted that when an element is referred to as being "fixed" to another element, it can be directly on the other element or one or more intermediate elements may be provided in between. When one element is referred to as being "connected" to another element, it can be directly connected to the other element or one or more intermediate elements may be provided in between. As used herein, the terms "upper", "lower", "inner", "outer", "bottom", and the like indicate orientations or positional relationships based on the orientation or positional relationships shown in the accompanying drawings. They are merely for the convenience in describing the present application and simplifying the description, and do not indicate or imply that the apparatus or element being referred to must have a particular orientation, or be constructed and operated in a particular orientation, and thus should not to be construed as limiting the present application. Furthermore, the terms "first", "second", "third" and the like are used for descriptive purposes only and are not to be construed as indicating or implying relative importance.

Unless defined otherwise, all technical and scientific terms used herein have the same meaning as commonly understood by one of ordinary skill in the art to which the present application belongs. The terms used in the description of the present application according to the description are to describe particular embodiments and are not intended to be limiting of the present application. As used herein, the term "and/or" includes any and all combinations of one or more of the associated listed items.

Furthermore, the technical features involved in different embodiments application described below can be combined with each other as long as they do not conflict with each other.

Figure 1:
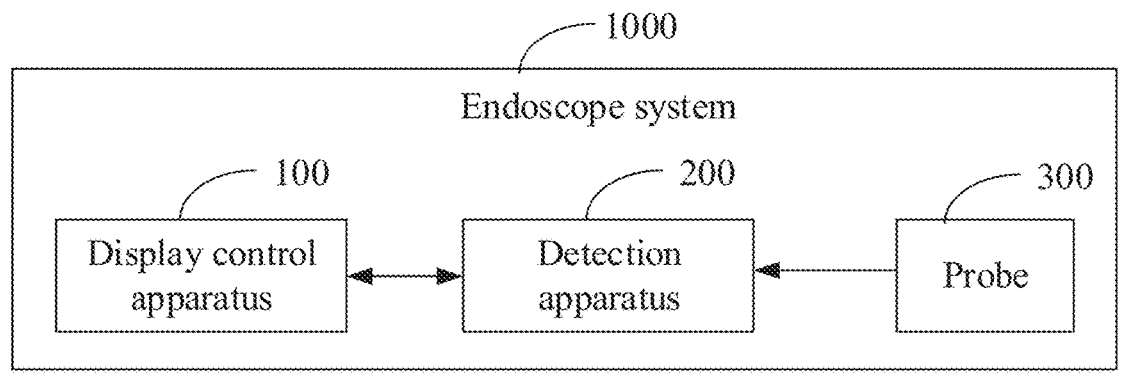
FIG. 1 is a schematic view showing a structure of an endoscope system provided by an embodiment of the present application.

Referring to FIG. 1, FIG. 1 is a schematic view showing a structure of an endoscope system provided by an embodiment of the present application. The endoscope system 1000 is applied to vehicle diagnosis equipments, mainly for fault diagnosis of a vehicle. The endoscope system 1000 includes: a display control apparatus 100, a detection apparatus 200, and a probe 300. The detection apparatus 200 is communicatively connected to the display control apparatus 100 and the probe 300, respectively.

The probe 300 is configured to collect image information of an internal device of a vehicle, the image information comprising pictures and/or videos. The probe 300 is further configured to transmit the image information to the detection apparatus 200, and the detection apparatus 200 is configured to forward the image information to the display control apparatus 100 to display the image information in the display control apparatus 100. In some embodiments, the detection apparatus 200 may process the image information, such as removing image noise, increasing image resolution, etc. before forwarding the image information to the display control apparatus 100, and the processed image information may be compressed and/or encrypted and then sent to the display control apparatus 100.

The display control apparatus 100 and the detection apparatus 200 can have a wireless communication connection or a wired communication connection therebetween such that when the display control apparatus 100 and the detection apparatus 200 communicate, data occupying a large memory space can be smoothly transmitted. The detection apparatus 200 and the probe 300 may be detachably connected, and the probe 300 is detachably fixed to the detection apparatus 200. When the two are connected, the probe 300 transmits data to the detection apparatus 200.

Figure 2:
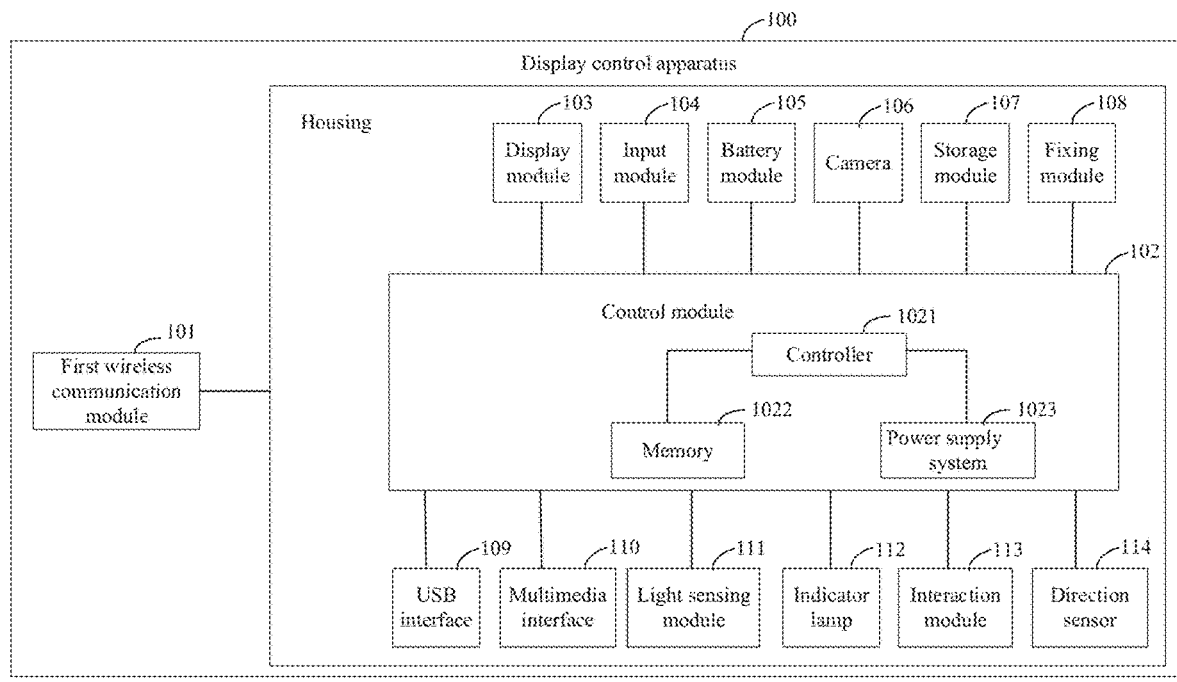
FIG. 2 is a schematic view showing the structure of a display control apparatus provided by an embodiment of the present application.

Referring to FIG. 2, the display control apparatus 100 includes a housing (not shown) in which a first wireless communication module 101, a control module 102, a battery module 105, a storage module 107, a light sensing module 111 and an direction sensor 114 are provided. The housing is provided with: a display module 103, an input module 104, a camera 106, a fixing module 108, a USB interface 109, a multimedia interface 110, an indicator lamp 112, and an interaction module 113.

The first wireless communication module 101, the display module 103, the input module 104, the battery module 105, the camera 106, the storage module 107, the USB interface 109, the multimedia interface 110, the light sensing module 111, the indicator lamp 112, the interaction module 113, and the direction sensor 114 are respectively electrically connected to the control module 102.

The first wireless communication module 101 may specifically be a WIFI module, a Bluetooth module, a ZigBee module, etc. When the first wireless communication module 101 is a WIFI module, the display control apparatus 100 is communicatively connected to the detection apparatus 200 via WIFI, and the WIFI module can be implemented based on 2.4G wireless technology or 5G wireless technology.

The control module 102 includes a controller 1021, a memory 1022, and a power supply system 1023. The controller 1021 and the memory 1022 may be connected via a bus or otherwise, and the power supply system 1023 is used to power the controller 1021.

The controller 1021 is any type of a single-threaded or multi-threaded controller having one or more processing cores. As a control core of the display control apparatus 100, the controller is configured to acquire data, execute logical operation functions, and issue an operation processing result. The memory 1022 includes non-volatile memory and volatile memory. The memory may have a program storage area for storing non-volatile software programs and non-volatile computer-executable programs, and for calling by the controller 1021 to cause the controller 1021 to execute one or more method steps. The memory 1022 may also have a data storage area for storing the operation processing result output and issued by the controller 1021.

In the present embodiment, the controller 1021 may in particular be a micro-control unit MCU, and the memory 1022 includes at least one, the memory including double rate synchronous dynamic random access memory (DDR SDRAM), non-volatile memory EMMC, etc. The DDR may be communicatively connected to the controller 1021 via a DDR bus and the EMMC may be communicatively connected to the controller 1021 via an EMMC bus.

In using the endoscope system 1000, the controller 1021 controls the display module 103 to display the image information after acquiring the image information sent by the detection apparatus 200.

The controller 1021 is also configured to acquire input information from the input module 104. The controller 1021 is further used to control the camera 106 to shoot the surrounding environment information where the display control apparatus 100 is currently located, and to acquire the environment information. The controller 1021 is also used to read or write data into the storage module 107. When the USB interface 109 is connected to third-party equipment, the controller 1021 is further used to transmit data, such as the image information, to the third-party equipment via the USB interface 109. The third-party equipment includes a personal computer, a notebook computer, etc. When the multimedia interface 110 is connected to third-party display equipment, the controller 1021 is further configured to output data to the third-party display equipment via the multimedia interface 110, such as displaying the image information on the third-party display equipment; the third-party display equipment can be a large-screen LED display screen, etc.; and the multimedia interface 110 can be an HDMI high-definition image transmission interface. The controller 1021 is also configured to acquire the ambient light brightness information collected by the light sensing module 111, adjust the screen brightness of the display module 103 according to the ambient light brightness information, and just the screen brightness of the touch screen when the input module 104 is a touch screen. The controller 1021 is also configured to control the working state of the indicator lamp 112 according to the state-of-charge of the battery module 105. For example, when the remaining battery level of the battery module 105 is less than a preset threshold value, the controller 1021 controls the indicator lamp 112 to be a red light; when the remaining battery level of the battery module 105 is greater than or equal to the preset threshold value, the controller 1021 controls the indicator lamp 112 to be a green light. The controller 1021 is also configured to acquire information collected by the interaction module 113, and the interaction module 113 is configured to realize the interaction between a user and the display control apparatus 100. The controller 1021 is also configured to acquire parameter information collected by the direction sensor 114, and adjust a display state of the display module 103 according to the parameter information, the display state including a screen display direction (such as a vertical screen display or a horizontal screen display), etc.

The display module 103 is located on the outer surface of the housing and is configured to display the image information, and the display module 103 may specifically be an LCD display screen. The display module 103 may simultaneously display at least two views, and at least two views may be freely switched.

The input module 104 is configured to receive an input operation of a user, and the input module 104 can be a touch screen, a touch keyboard, a voice input module (such as a microphone, etc.), a physical key, etc. A user may input information, such as inquiring image information or the like, into the display control apparatus 100 by operating the input module 104.

The battery module 105 is configured to supply power to the display control apparatus 100. The battery module 105 may be a large-capacity rechargeable lithium battery to ensure that the electric quantity of the display control apparatus 100 can last longer while allowing the battery of the display control apparatus 100 to be reused.

The camera 106 is configured to collect information of the environment where the display control apparatus 100 is currently located. The site conditions at the time of vehicle diagnosis can be recorded by the camera 106.

The storage module 107 is configured to store the image information. The storage module 107 can specifically be a TF card, and can realize a large data storage of more than 32 Gbit.

The fixing module 108 is provided on the outer surface of the housing, and the fixing module 108 is configured to fix the display control apparatus 100. The fixing module 108 may specifically be a magnet, and at least one is included. The magnet is attached to a metal surface, thereby fixing the display control apparatus 100.

The USB interface 109 is configured to realize that the display control apparatus 100 is connected to third-party equipment so that the third-party equipment reads data, such as copying the image information, via the USB interface 109. The number of the USB interfaces 109 is not particularly limited and may be one or more.

The multimedia interface 110 is configured to connecting third-party display equipment, and the multimedia interface 110 can specifically be an HDMI high-definition image output port, and the third-party display equipment can be a large-screen LED display screen. The display control apparatus 100 is connected to third-party display equipment via the multimedia interface 110 so that the collected image can be placed on a high-definition display for magnified observation, so as to facilitate finding the cracks, wear, blockages and suspicious components, and provide original materials for non-destructive analysis of failure causes. When image information is displayed on the third-party display equipment, 1 million pixels high-definition imaging can be realized, and the image can be freely zoomed.

The light sensing module 111 is configured to detect the ambient light brightness so that the control module 102 adjusts the screen brightness of the display module 103 according to the ambient light brightness to present an image effect more clearly.

The indicator lamp 112 is configured to remind a user of the state-of-charge of the battery module 105, and perform a preset reaction according to the current battery level of the battery module 105. For example, when the remaining battery level of the battery module 105 is less than a preset threshold value, the indicator lamp 112 is a red light; when the remaining battery level of the battery module 105 is greater than or equal to the preset threshold value, the indicator lamp 112 is a green light. By means of the working state of the indicator lamp 112, the user can learn the battery level information of the display control apparatus 100 in time, so as to charge in time and ensure a smooth vehicle diagnosis process.

The interaction module 113 is configured to realize the interaction between the display control apparatus 100 and a user. The interaction module 113 specifically comprises a microphone, a loudspeaker, etc. and the user can realize voice interaction with the display control apparatus 100 via the microphone and the loudspeaker. When the user inputs voice information, the control module 102 performs voice recognition and analysis on the voice information so as to react accordingly.

The direction sensor 114 is configured to detect the display state of the display module 103. Specifically, the direction sensor 114 detects the display direction of the screen, and adjust the screen display angle according to the screen display direction and the size of the image to be displayed, so that the displayed image has a good display effect.

The display control apparatus 100 provided by an embodiment of the present application is mainly configured to display the image information collected by the probe 300, and can acquire data from a long distance to facilitate the mobile operation of the equipment, and can conveniently and quickly store and read images and video files and magnify and display the read images and video on a large screen in a high-definition, which provides assistance for a technician to diagnose a fault.

Figure 3:
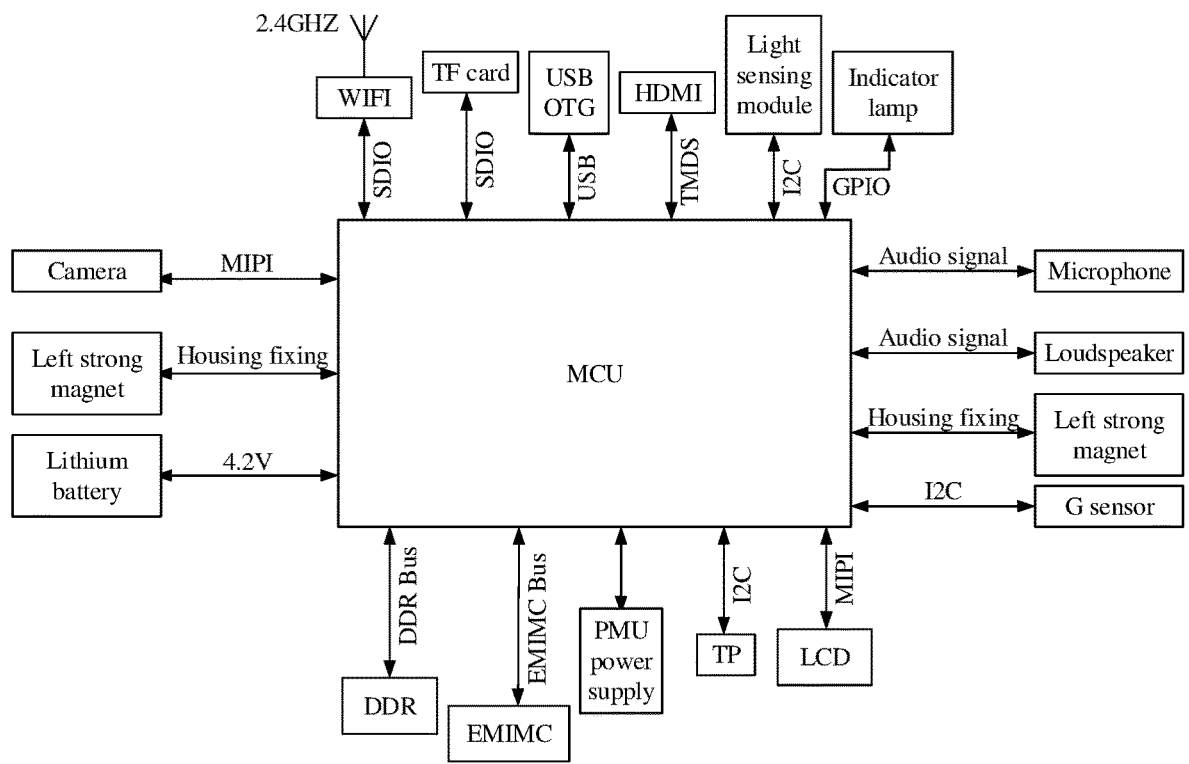
FIG. 3 is a schematic view showing the structure of a display control apparatus provided by another embodiment of the present application.

It should be noted that the display control apparatus 100 can be specifically shown in FIG. 3. The display control apparatus 100 comprises an MCU, a DDR, an EMMC, a PMU power supply, a TP touch screen, an LCD display screen, a WIFI module, a TF card, a USB OTG interface, an HDMI interface, a light sensing module, an indicator lamp, a camera, a lithium battery, a microphone, a loudspeaker, a direction sensor, and a left strong magnet and a right strong magnet. The DDR and EMMC are respectively connected to the MCU via a bus, and the MCU, DDR, EMMC and PMU power supply constitute one small system as the core of the display control apparatus 100. The WIFI module, TF card, USB OTG interface, HDMI interface, light sensing module, indicator lamp, camera, lithium battery, microphone, loudspeaker and direction sensor are respectively electrically connected to the MCU. The left strong magnet and right strong magnet are arranged on the housing of the display control apparatus 100, and the display control apparatus 100 is movably fixed by means of magnet adsorption. The TP touch screen, direction sensor, and light sensing module are all connected to the MCU via an I2C bus, the LCD display screen and the camera are both connected to the MCU via a MIPI bus, the WIFI module and TF card are both connected to the MCU via an SDIO bus, the HDMI interface communicates with the MCU based on a TMDS protocol, and the indicator lamp is connected to the MCU via a GPIO interface. The microphone is configured to transmit an audio signal to the MCU, and the loudspeaker is configured to read the audio signal sent by the MCU. It needs to be noted that FIG. 3 is merely an example of the display control apparatus 100, and is not intended to limit the display control apparatus 100.

Figure 4:
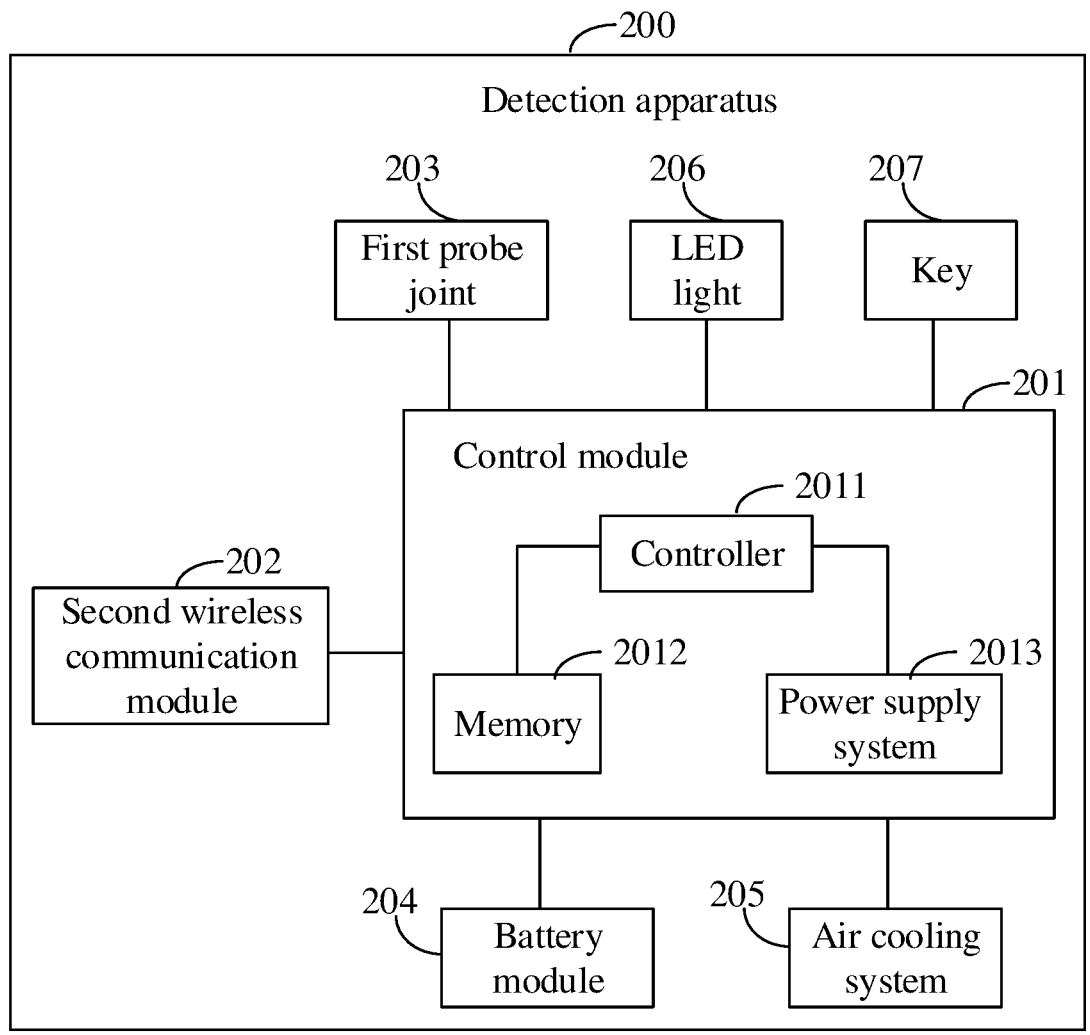
FIG. 4 is a schematic view showing the structure of a detection apparatus provided by an embodiment of the present application.

Referring to FIG. 4, the detection apparatus 200 includes a control module 201, a second wireless communication module 202, a first probe joint 203, a battery module 204, an air cooling system 205, an LED light 206, and a key 207. The second wireless communication module 202, the first probe joint 203, the battery module 204, the air cooling system 205, the LED light 206, and the key 207 are electrically connected to the control module 201, respectively.

The control module 201 includes a controller 2011, a memory 2012, and a power supply system 2013.

The controller 2011 is any type of single-threaded or multi-threaded controller having one or more processing cores. As a control core of the detection apparatus 200, the controller is configured to acquire data, executing logical operation functions, and issue an operation processing result. The memory 2012 includes non-volatile memory and volatile memory. The memory may have a program storage area for storing non-volatile software programs and non-volatile computer-executable programs, and for calling by the controller 2011 to cause the controller 2011 to execute one or more method steps. The memory 2012 may also have a data storage area for storing the operation processing result output and issued by the controller 2011.

In the present embodiment, the controller 2011 may specifically be a micro-control unit MCU, and the memory 2012 includes at least one, the memory including double rate synchronous dynamic random access memory (DDR SDRAM), flash memory (flash), etc. The DDR may be communicatively connected to the controller 2011 via a DDR bus and the flash may be communicatively connected to the controller 2011 via an SPI bus.

The controller 2011 is configured to acquire image information collected by the probe 300 via the first probe joint 203, and forward the image information to the display control apparatus 100 via the second wireless communication module 202. The controller 2011 is further configured to control the working state of the air cooling system 205 according to the service time of the equipment or the current working temperature of the equipment. For example, when the working time of the equipment is greater than a preset threshold value or the temperature of the equipment is higher than a preset temperature, the air cooling system 205 is controlled to be turned on to cool the equipment and make the equipment work more reliably. The controller 2011 is further configured to control the working state of the LED light 206, and whether to turn on the LED light 206 can be selected according to the brightness of the current working environment of the equipment. The controller 2011 may also be configured to detect an electrical signal of the key 207 and respond to the electrical signal. For example, the controller 2011 toggles the key 207 up to photograph and toggles the key 207 down for camera shooting. The controller 2011 reacts differently by detecting an electrical signal generated when a key is toggled.

The second wireless communication module 202 may specifically be a WIFI module, a Bluetooth module, a ZigBee module, etc. When the second wireless communication module 202 is a WIFI module, the detection apparatus 200 is communicatively connected to the display control apparatus 100 via WIFI, and the WIFI module can be implemented based on 2.4G wireless technology or 5G wireless technology.

The first probe joint 203 is configured to communicate the probing apparatus 200 with the probe 300. The first probe joint 203 may specifically be a USB interface, and the number of USB interfaces may be one or more.

The battery module 204 is configured to supply power to the detection apparatus 200. The battery module 204 may be a high capacity rechargeable lithium battery to ensure that the electric quantity of the detection apparatus 200 can last longer while allowing the battery of the detection apparatus 200 to be reused.

The air cooling system 205 is configured to provide a cooling service for the detection apparatus 200. The air cooling system 205 can be used to cool the detection apparatus 200 when the detection apparatus 200 works for a long time or the temperature of the detection apparatus 200 is too high.

The LED light 206 is configured to provide ambient lighting. The number of the LED lights 206 is not specifically limited and includes one or more.

The key 207 is configured to receive a user's operation so as to realize interactive functions such as photographing, video recording, and storing. The key 207 may be a real physical key provided on the detection apparatus 200 or a virtual key on a touch screen. The key 207 includes at least one. Different operations executed by the key 207 respectively correspond to different interactive functions, for example, toggling the key 207 up to photograph, toggling the key 207 down for camera shooting, etc. The control module 201 may be responsive to an operation of the key 207 by the user.

Figure 5:
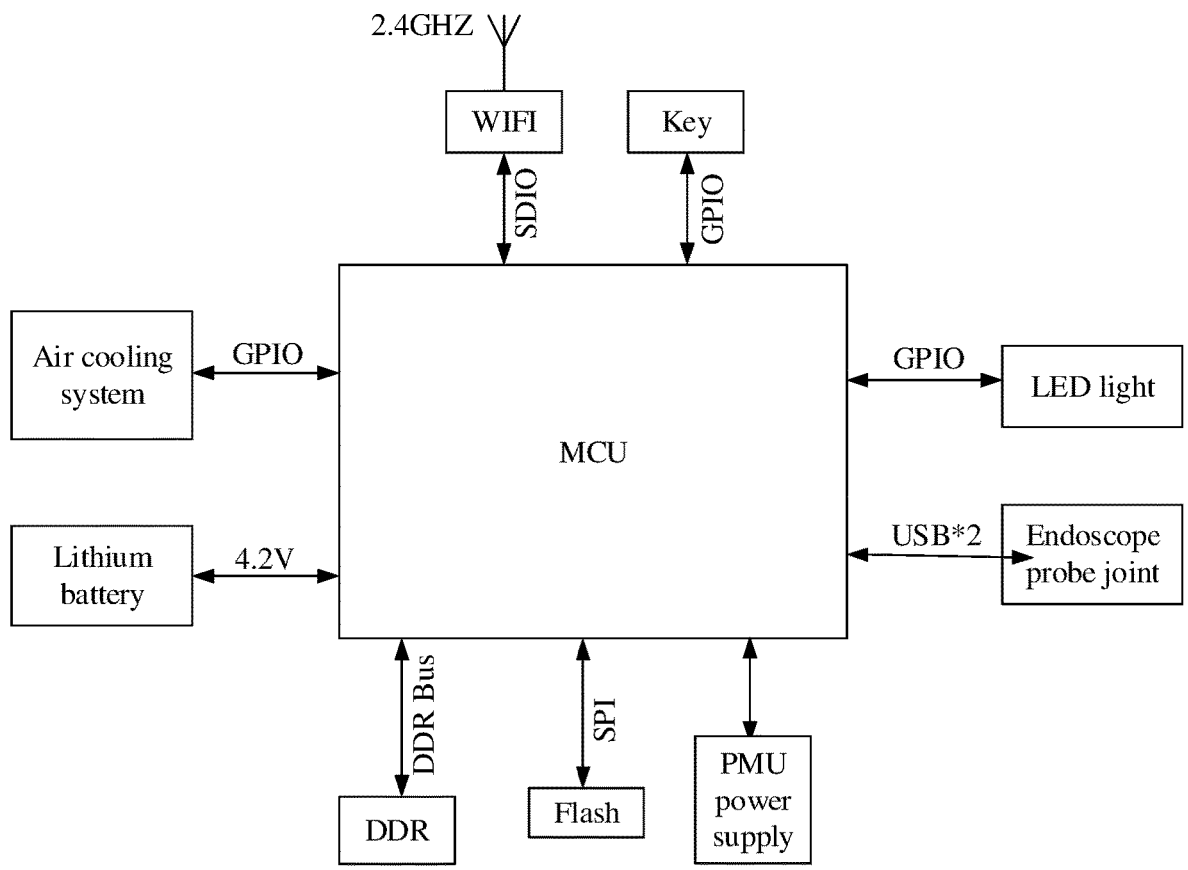
FIG. 5 is a schematic view showing the structure of a detection apparatus provided by another embodiment of the present application.

It should be noted that the detection apparatus 200 can specifically be as shown in FIG. 5. The detection apparatus 200 comprises an MCU, a DDR, a Flash, a PMU power supply, a WIFI module, an air cooling system, a lithium battery, an LED light, and an endoscope probe joint. The DDR memory is communicatively connected to the MCU via the DDR bus, the Flash is communicatively connected to the MCU via the SPI bus, the air cooling system, the LED light, and the key are all connected to the MCU based on the GPIO interface, the WIFI module is communicatively connected to the MCU based on the SDIO bus, the endoscope probe joint can specifically be a USB interface, and the lithium battery can provide a power supply voltage of 4.2V.

It should be noted that FIG. 5 is merely an example of the detection apparatus 200 and is not intended to limit the detection apparatus 200.

Figure 6:
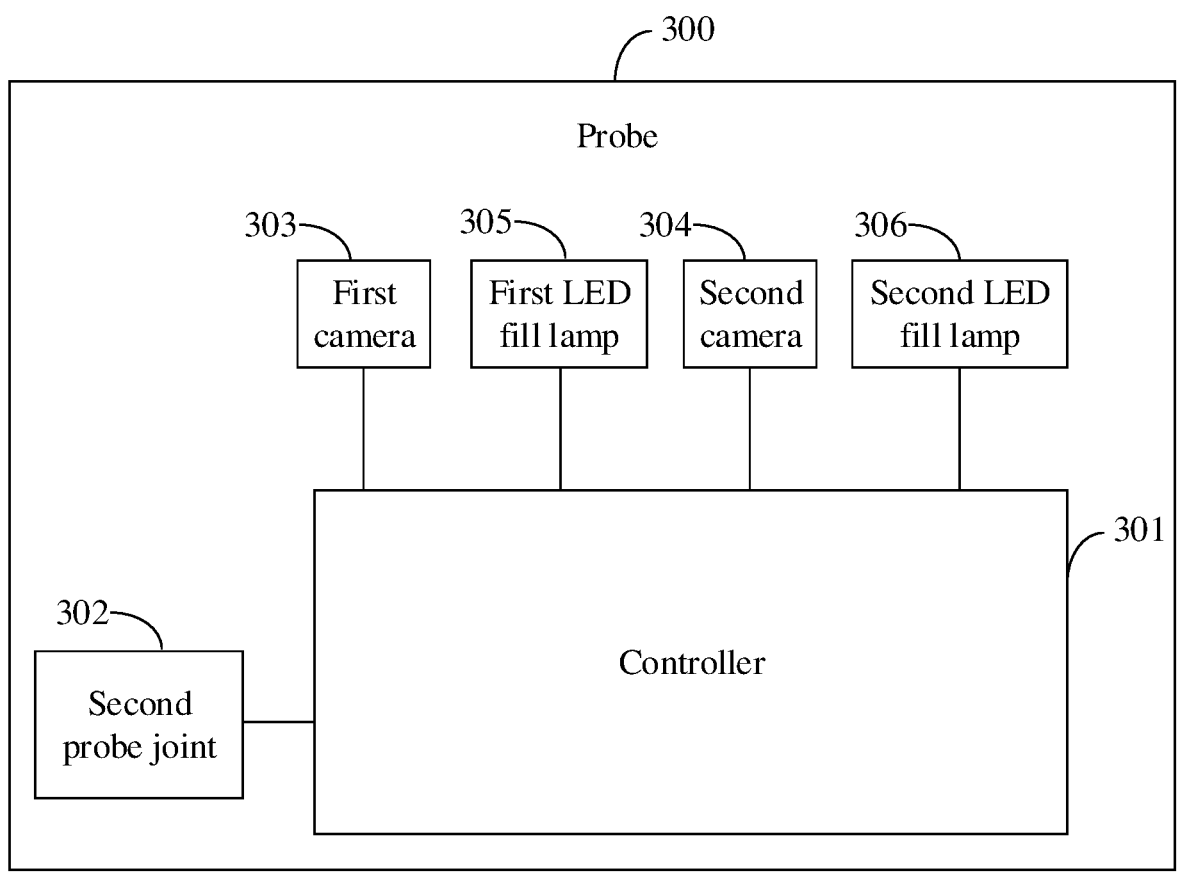
FIG. 6 is a schematic view showing the structure of a probe provided by an embodiment of the present application.

Referring to FIG. 6, the probe 300 includes: a controller 301, a second probe joint 302, a first camera 303, a second camera 304, a first LED fill lamp 305, and a second LED fill lamp 306. The controller 301 is electrically connected to the first camera 303, the second camera 304, the first LED fill lamp 305, the second LED fill lamp 306, and the second probe joint 302, respectively. The controller 301 is configured to control the first camera 303 and the second camera 304 to collect the image information, adjust the brightness of the first LED fill lamp 305 and the second LED fill lamp 306 according to the environment, and transmit the image information to the detection apparatus 200 via the second probe joint 302.

The first camera 303 can be at the front end of the probe head so as to achieve image acquisition of a front scene, and the second camera 304 can be arranged at the side end of the probe head so as to achieve 360-degree panoramic image acquisition of a side, and the two cameras can be displayed simultaneously. The first LED fill lamp 305 can serve as a fill lamp of the first camera 303, and the second LED fill lamp 306 can serve as a fill lamp of the second camera 304, so as to realize image collection operation under any light environment.

The second probe joint 302 is configured to connect to the first probe joint 203 in the detection apparatus 200 so as to transmit the filmed digital video signal. The second probe joint 302 may be a USB receptacle when the first probe joint 203 is a USB interface or may be a USB interface when the first probe joint 203 is a USB receptacle.

The probe 300 may specifically be made of a detachable circular flexible material so as to be able to bend at any angle to facilitate detecting.

In the present embodiment, the detection apparatus 200 can send a control instruction to the probe 300 via the first probe joint 203 and the second probe joint 302. The controller 301 of the probe 300 responds to the control instruction, controls two cameras to collect the image information according to the control instruction, and returns the collected image information to the detection apparatus 200 via the two probe joints. The detection apparatus 200 sends the image information to a display control apparatus 100 via a wireless communication module so that the image information is displayed on the display control apparatus 100 for a technician to perform failure analysis and diagnosis of a vehicle according to the image information.

It should be noted that, in addition to the communication connection with the display control apparatus 100, the detection apparatus 200 can also be connected to the upper computer of the vehicle fault diagnosis system through WIFI, or connected to a PC computer, or connected to a smart phone, etc., so as to realize the respective convenient mobile endoscope detection.

Different from the prior art, the endoscope system provided by the embodiments of the present application is capable of performing 360-degree panoramic detection in the front and on the side with a large imaging viewing angle when collecting image information, wherein the probe can be bent at any angle to freely adjust the detection position; when the image information is transmitted, the video signal can be transmitted over a long distance of more than 100 meters; when displaying the image information, one screen can simultaneously display the images of two cameras, and the two views can be freely switched; furthermore, high-pixel high-definition imaging can also be realized, and HDMI high-definition video projection can also be realized. The endoscope system according to the embodiments of the present application realizes the separate operation of image collection and image display, can conveniently and quickly store and read image information, and realizes a convenient, accurate, and highly efficient vehicle fault diagnosis operation while facilitating mobile operation thereof.

Finally, it should be noted that: the above embodiments are merely illustrative of the technical solutions of the present application, rather than limiting it; combinations of technical features in the above embodiments or in different embodiments are also possible under the idea of the present application, and the steps can be implemented in any order; there are many other variations of the different aspects of the present application as described above, which are not provided in detail for the sake of brevity; although the present application has been described in detail with reference to the foregoing embodiments, those of ordinary skills in the art will appreciate that the technical solutions disclosed in the above-mentioned embodiments can still be modified, or some of the technical features thereof can be replaced by equivalents; such modifications or replacements do not depart the essence of the corresponding technical solution from the scope of the technical solutions of embodiments of the present application.

What is claimed is:

1. An endoscope system applied to vehicle diagnosis equipment, the endoscope system comprising a display control apparatus, a detection apparatus, and a probe, the detection apparatus being communicatively connected with the display control apparatus and the probe respectively;
   the probe being configured to collect image information of an internal device of a vehicle and sending the image information to the detection apparatus;
   the detection apparatus being configured to send the image information to the display control apparatus; and
   the display control apparatus being configured to display the image information;
   wherein the display control apparatus comprises a first wireless communication module, and the detection apparatus comprises a second wireless communication module and a first probe joint, the display control apparatus being communicatively connected to the second wireless communication module of the detection apparatus via the first wireless communication module, and the detection apparatus being communicatively connected to the probe via the first probe joint;
   wherein the detection apparatus further comprises a control module, the control module being connected to the first probe joint and configured to acquire the image information via the first probe joint;
   wherein the detection apparatus further comprises a battery module, an air cooling system, an LED light, and a key, wherein:
   the battery module, the air cooling system, the LED light, and the key are respectively electrically connected to the control module; and
   the battery module is configured to supply power to the detection apparatus, the air cooling system is configured to provide a cooling service for the detection apparatus, the LED light is configured to provide ambient lighting, and the key is configured to receive an operation of a user to realize interactive functions of photographing, video recording, and storing.

2. The endoscope system according to claim 1, wherein the first wireless communication module and the second wireless communication module are WIFI modules, and the first probe joint is a USB interface.

3. The endoscope system according to claim 2, wherein the probe is provided with a first camera and a second camera, the first camera being correspondingly provided with an LED fill lamp, and the second camera being correspondingly provided with another LED fill lamp, wherein:
   the probe further comprises a controller and a second probe joint, the controller is respectively electrically connected to the first camera, the second camera, two LED fill lamps, and the second probe joint; and
   the controller is configured to control the first camera and the second camera to collect the image information, adjust the brightness of the two LED fill lamps according to the environment, and transmit the image information to the detection apparatus via the second probe joint.

4. The endoscope system according to claim 3, wherein the display control apparatus comprises a housing, a control module is provided in the housing, and a display module is provided on the housing, the control module being electrically connected to the display module;
   the control module being configured to control the display module to display the image information.

5. The endoscope system according to claim 4, wherein the control module comprises a controller, a memory, and a power supply system;
   the memory being communicatively connected to the controller via a bus, and the power supply system being electrically connected to the controller; and
   the controller being configured to control the display module to display the image information sent by the detection apparatus.

6. The endoscope system according to claim 5, wherein the probe is provided with a first camera and a second camera, the first camera being correspondingly provided with an LED fill lamp, and the second camera being correspondingly provided with another LED fill lamp, wherein:
   the probe further comprises a controller and a second probe joint, the controller is respectively electrically connected to the first camera, the second camera, two LED fill lamps, and the second probe joint; and
   the controller is configured to control the first camera and the second camera to collect the image information, adjust the brightness of the two LED fill lamps according to the environment, and transmit the image information to the detection apparatus via the second probe joint.

7. The endoscope system according to claim 4, wherein the display control apparatus further comprises an input module, a battery module, a fixing module, a camera, a storage module, a USB interface, a multimedia interface, a light sensing module, an indicator lamp, an interaction module, and a direction sensor; wherein:
   the battery module, the storage module, the light sensing module, and the direction sensor are arranged in the housing and are respectively electrically connected to the control module, the fixing module is arranged on an outer surface of the housing, the input module, the camera, the USB interface, the multimedia interface, the indicator lamp, and the interaction module are arranged on the housing and are electrically connected to the control module respectively;
   the input module is configured to receive an input operation of a user, the battery module is configured to supply power to the display control apparatus, the fixing module is configured to fix the display control apparatus, the camera is configured to collect information of an environment where the display control apparatus is currently located, the storage module is configured to store the image information, the USB interface is configured to transmitting the image information to third-party equipment, the multimedia interface is configured to connect third-party display equipment, the light sensing module is configured to detect brightness of ambient light, the indicator lamp is configured to remind the user of state-of-charge of the battery module, the interaction module is configured to realize interaction between the display control apparatus and the user, and the direction sensor is configured to detect a display state of the display module.

8. The endoscope system according to claim 7, wherein the probe is provided with a first camera and a second camera, the first camera being correspondingly provided with an LED fill lamp, and the second camera being correspondingly provided with another LED fill lamp, wherein:
the probe further comprises a controller and a second probe joint, the controller is respectively electrically connected to the first camera, the second camera, two LED fill lamps, and the second probe joint; and
the controller is configured to control the first camera and the second camera to collect the image information, adjust the brightness of the two LED fill lamps according to the environment, and transmit the image information to the detection apparatus via the second probe joint.

9. The endoscope system according to claim 4, wherein the probe is provided with a first camera and a second camera, the first camera being correspondingly provided with an LED fill lamp, and the second camera being correspondingly provided with another LED fill lamp, wherein:
the probe further comprises a controller and a second probe joint, the controller is respectively electrically connected to the first camera, the second camera, two LED fill lamps, and the second probe joint; and
the controller is configured to control the first camera and the second camera to collect the image information, adjust the brightness of the two LED fill lamps according to the environment, and transmit the image information to the detection apparatus via the second probe joint.

10. The endoscope system according to claim 1, wherein the control module comprises a controller, a memory, and a power supply system, the memory being communicatively connected to the controller via a bus, and the power supply system being electrically connected to the controller.

11. The endoscope system according to claim 10, wherein the probe is provided with a first camera and a second camera, the first camera being correspondingly provided with an LED fill lamp, and the second camera being correspondingly provided with another LED fill lamp, wherein:
the probe further comprises a controller and a second probe joint, the controller is respectively electrically connected to the first camera, the second camera, two LED fill lamps, and the second probe joint; and
the controller is configured to control the first camera and the second camera to collect the image information, adjust the brightness of the two LED fill lamps according to the environment, and transmit the image information to the detection apparatus via the second probe joint.

12. The endoscope system according to claim 1, wherein the probe is provided with a first camera and a second camera, the first camera being correspondingly provided with an LED fill lamp, and the second camera being correspondingly provided with another LED fill lamp, wherein:
the probe further comprises a controller and a second probe joint, the controller is respectively electrically connected to the first camera, the second camera, two LED fill lamps, and the second probe joint; and
the controller is configured to control the first camera and the second camera to collect the image information, adjust the brightness of the two LED fill lamps according to the environment, and transmit the image information to the detection apparatus via the second probe joint.

* * * * *